US012564649B2

(12) United States Patent
Guo et al.

(10) Patent No.: US 12,564,649 B2
(45) Date of Patent: Mar. 3, 2026

(54) INTERFACE MATERIAL FOR VIRTUAL REALITY INTERACTION AND PREPARATION METHOD THEREFOR

(71) Applicant: Shanghai Wearalab Co., Ltd., Shanghai (CN)

(72) Inventors: Yang Guo, Shanghai (CN); Zhifu Liu, Shanghai (CN)

(73) Assignee: Shanghai Wearalab Co., Ltd., Shanghai (CN)

( * ) Notice: Subject to any disclaimer, the term of this patent is extended or adjusted under 35 U.S.C. 154(b) by 836 days.

(21) Appl. No.: 17/816,119

(22) Filed: Jul. 29, 2022

(65) Prior Publication Data

US 2023/0211019 A1 Jul. 6, 2023

(30) Foreign Application Priority Data

Jan. 4, 2022 (CN) .......................... 202210002827.0

(51) Int. Cl.

| | |
|---|---|
| *A61K 49/00* | (2006.01) |
| *C08J 3/075* | (2006.01) |
| *C08K 5/1545* | (2006.01) |
| *G06F 3/01* | (2006.01) |

(52) U.S. Cl.
CPC ............... *A61K 49/00* (2013.01); *C08J 3/075* (2013.01); *G06F 3/015* (2013.01); *C08J 2333/26* (2013.01); *C08K 5/1545* (2013.01)

(58) Field of Classification Search
CPC ....... A61K 49/00; C08J 3/075; C08J 2333/26; G06F 3/015; G06F 3/011; G06F 3/017; C08K 5/1545
See application file for complete search history.

(56) References Cited

PUBLICATIONS

Machine English translation of CN 111234112 (Year: 2020).*
Machine English translation of CN 113801265 (Year: 2021).*

* cited by examiner

*Primary Examiner* — Jessica M Roswell
(74) *Attorney, Agent, or Firm* — Ryan L. Marshall; Barnes & Thornburg LLP

(57) ABSTRACT

The present disclosure relates to an interface material for virtual reality interaction and a preparation method therefor. The interface material is composed of an ionic conductive self-adhesive hydrogel and an organic solvent. The preparation method includes: (1) preparing a prepolymer solution; (2) preparing a bioelectrical sensing pregel by ultraviolet (UV) curing; and (3) preparing an interface material for virtual reality interaction by solvent extraction. The preparation method of the present disclosure is simple and cost-effective, and can be used for large-scale production. The obtained gel interface material has excellent properties such as high stability, high sensitivity, non-invasiveness, and reusability, can be used for detection of bioelectrical signals such as electromyography (EMG) signals and electroencephalography (EEG) signals, and has important application value in the field of virtual reality interaction.

10 Claims, 6 Drawing Sheets

INTERFACE MATERIAL FOR VIRTUAL REALITY INTERACTION AND PREPARATION METHOD THEREFOR

RELATED APPLICATION

This application claims priority to CN application no. 202210002827.0, filed Jan. 4, 2022. The disclosure of this priority application is incorporated herein in its entirety.

TECHNICAL FIELD

The present disclosure belongs to the field of human-computer interaction, and in particular, relates to a bioelectrical signal sensing interface material for virtual reality interaction.

BACKGROUND ART

The metaverse can build a virtual world parallel to the real world for human beings, while corresponding interface materials need to be developed for virtual reality interaction. As the basis of biological activities, medical diagnosis and treatment, and neuroscience, bioelectrical signals are the basis for in-depth understanding of the laws and pathological mechanisms of biological activities. Detection methods are crucial in the in-depth study of the bioelectrical signals.

However, the current bioelectrical signal detection methods face many challenges. As a general high-precision detection method, invasive electrodes are widely used. For example, the Chinese patent CN202011078894.8 prepares an invasive electrode for acquiring neural signals. However, the invasive electrodes also have the following shortcomings: (1) the discomfort caused by the invasion makes invasive electrodes unable to perform long-term detection, (2) the wound caused by the invasion can trigger an immune response, and form a scar/biofilm interface, and (3) the invasive electrodes are mostly needle-shaped, and the obtained signal range is relatively small. These defects limit the use of invasive electrodes. Therefore, the use of non-invasive electrodes is imperative.

Dry electrodes have been widely studied as non-invasive electrodes. For example, the Chinese patent CN201921164026.4 prepares an anti-interference flexible bioelectricity dry electrode. However, due to the existence of skin folds, the dry electrode cannot fully fit the skin, thus forming a gap between the electrode and the skin. Therefore, during the movement, the gap will change, resulting in unstable signal quality of the dry electrode. In addition, the dry electrodes lack sufficient electrolyte, resulting in extremely high electrode-skin interface impedance (>100 kΩ). These defects make the quality of bioelectrical signals obtained by the dry electrodes extremely poor. Therefore, the development of wet electrodes as flexible and high-conductivity bioelectrical sensing materials has received increasing attention.

The wet electrodes use electrolyte-rich gel-like materials as electrode-skin interfaces (like existing commercial electrodes), and are commonly used in clinical diagnostics and scientific research due to the low interface impedance obtained. However, the existing wet electrodes have insufficient performance for reuse, and the gel loses water and dries out over time, resulting in a sharp drop in signal quality. Therefore, it is particularly urgent to upgrade the bioelectrical sensing materials.

Due to the excellent electrical conductivity, flexibility, biocompatibility, and shape/structure designability, ionic conductive hydrogels have been widely used as biorobots, biosensors, electronic skins, and brain-computer interface materials. However, the existing ionic conductive hydrogels still face some challenges, such as lack of viscosity, insufficient water retention, mismatching with skin mechanical properties, and low transmission efficiency of electrical signals. The ionic conductive organohydrogels have received increasing attention due to excellent water retention and environmental adaptability, for example: organohydrogel-based strain sensors (ACS Appl. Mater. Interfaces 2021, 13, 1474-1485); organohydrogel-based ionic microdevices (ACS Appl. Mater. Interfaces 2020, 12, 56393-56402); and organohydrogel for ionic skins (Chem. Eng. J. 2021, 404, 126559). The above work also provides ideas for the application of ionic conductive organohydrogels in the field of bioelectrical sensing.

SUMMARY

A technical problem to be solved by the present disclosure is to provide an interface material for virtual reality interaction and a preparation method therefor, so as to overcome the defects that existing commercial electrodes cannot be reused and invasive electrodes can cause damage to living organisms.

The present disclosure provides an interface material for virtual reality interaction, uses a hydrogel with excellent biocompatibility as a base to obtain a low modulus, and introduces a reversible chemical bond to improve elasticity and optimize skin compliance. An organic solvent is used to improve water retention, and after disinfection with 75% ethanol, the detection performance is stable, making the interface material reusable. Based on the ion transport theory of bioelectrical signals, alkali metal salt is added to improve ionic conductivity. Tannic acid is added to impart viscosity and avoid electrode-skin gaps, resulting in high bioelectrical sensitivity and low interface impedance.

Ultraviolet (UV) curing is to conduct irradiation with a UV lamp and synthesize a pregel. Raw materials used are acrylamide, sodium chloride, tannic acid, a photoinitiator 12959 (2-hydroxy-1-[4-(2-hydroxyethoxy)phenyl]-2-methylpropan-1-one), and a crosslinking agent N-isopropylacrylamide. The synthesized pregel is ion-conducting polymer and self-adhesion.

Solvent extraction is to soak the pregel in an organic solvent for solvent extraction. The organic solvent used is ethylene glycol.

The present disclosure further provides a preparation method for the disinfectable and high-sensitivity interface material for virtual reality interaction, including:

(1) preparing a prepolymer solution: dissolving a gel monomer, alkali metal salt, tannic acid, a photoinitiator 12959, and a crosslinking agent methylenebisacrylamide in an aqueous solution to prepare the prepolymer solution;

(2) implementing UV curing: pouring the prepolymer solution obtained in step (1) into a mold, and conducting illumination under a UV lamp to prepare a pregel; and (3) implementing solvent extraction: soaking the pregel obtained in step (2) in an organic solvent for solvent extraction to obtain the interface material for virtual reality interaction.

In step (1), the gel monomer may be one or more selected from the group consisting of acrylamide, acrylic acid, sodium acrylate, and N-isopropylacrylamide. The alkali metal salt may be one or more selected from the group consisting of lithium chloride, sodium chloride, and potassium chloride. The gel monomer may have a concentration of 1-5 mol/L in the aqueous solution. The alkali metal salt may have a concentration of 0.1-3 mol/L in the aqueous solution. The tannic acid may have a concentration of 0.5-3 g/L in the aqueous solution.

In step (2), the irradiation may be conducted at a UV lamp wavelength of 305-395 nm and a power of 20-200 W for 3-60 min.

In step (3), the organic solvent may be one or more selected from the group consisting of ethylene glycol, glycerol, and dimethyl sulfoxide. The soaking may be conducted for 1-24 h.

The interface material for virtual reality interaction prepared by the present disclosure is capable of being reused after disinfection with 75% ethanol, is a non-invasive interface material, and has excellent sensitivity and stability.

Beneficial Effects (1) The shortcomings of traditional commercial electrode materials are overcome: traditional commercial electrodes are disposable consumables. However, the interface material for virtual reality interaction of the present disclosure can obtain accurate electrocardiography (ECG) signals after 60 days of detection. After 100 times of disinfection, the quality of ECG signals is still stable.

(2) Microvolt-level bioelectrical signal detection sensitivity: in the clinical auditory brainstem response test, the interface material for virtual reality interaction of the present disclosure is used for non-invasive detection to obtain the same sensitivity (microvolt level) as that of invasive electrodes.

DETAILED DESCRIPTION OF THE EMBODIMENTS

The present disclosure will be described in detail below with reference to specific examples. It should be understood that these examples are only intended to describe the present disclosure, rather than to limit the scope of the present disclosure. In addition, it should be understood that various changes and modifications may be made on the present disclosure by those skilled in the art after reading the content of the present disclosure, and these equivalent forms also fall within the scope defined by the appended claims of the present disclosure.

Example 1

(1) At a room temperature, 2 g of acrylamide powder was weighed and placed into a 100 mL beaker. 10 mL of deionized water was added. 0.8 g of sodium chloride, 0.1 g of tannic acid, 0.005 g of methylenebisacrylamide, and 0.05 g of a photoinitiator 12959 were added in sequence. Magnetic stirring was conducted for 1 h to obtain a transparent and clear prepolymer solution.

(2) The prepolymer solution obtained in step (1) was placed under a UV lamp with a wavelength of 365 nm and a power of 45 W for 20 min to obtain a pregel.

(3) The pregel obtained in step (2) was soaked in ethylene glycol for 1 h to obtain an interface material for virtual reality interaction.

Figure 1:
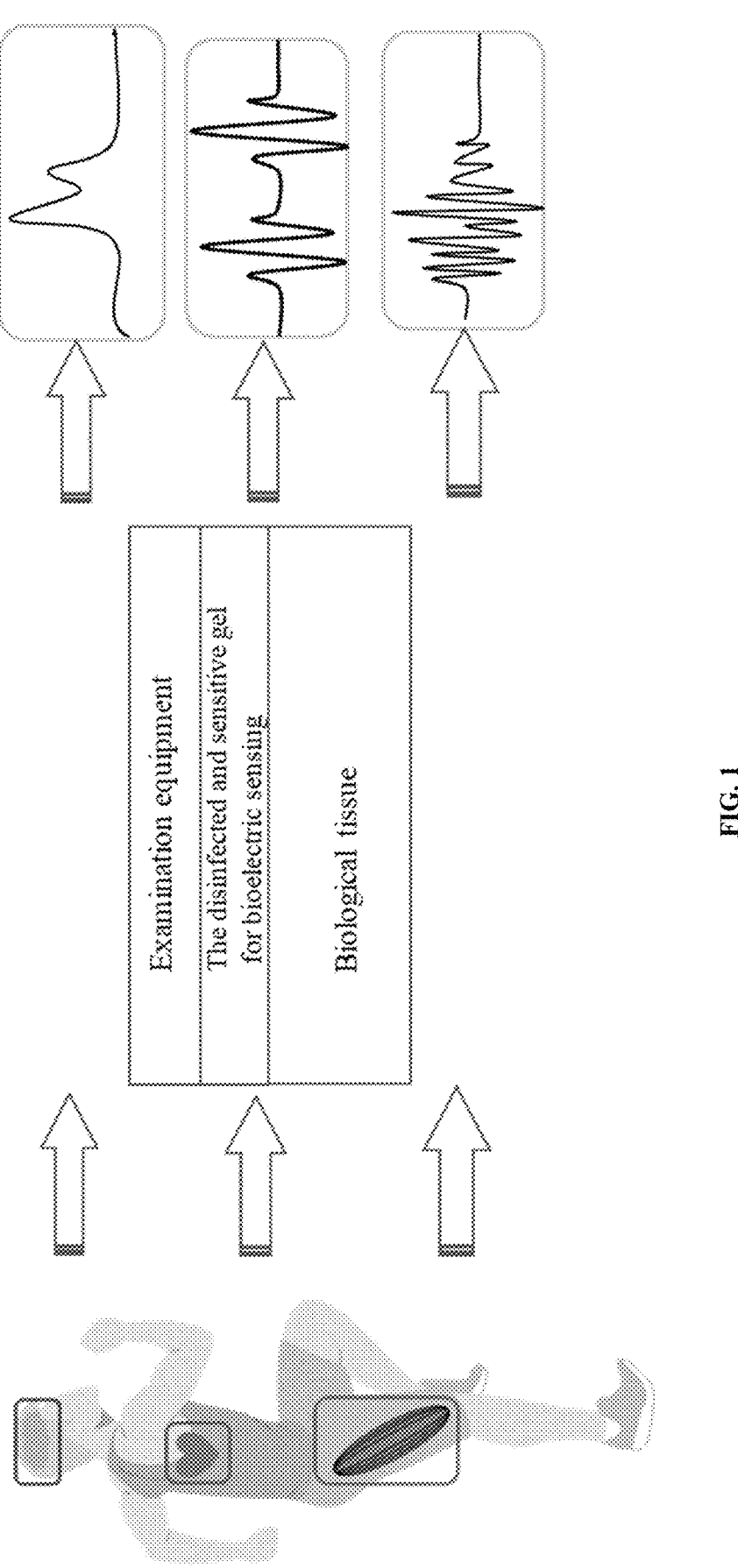
FIG. 1 is a schematic diagram of a bioelectrical signal sensing function of an interface material for virtual reality interaction prepared by the present disclosure, including electroencephalography (EEG) signals, ECG signals, and electromyography (EMG) signals.
Figure 2:
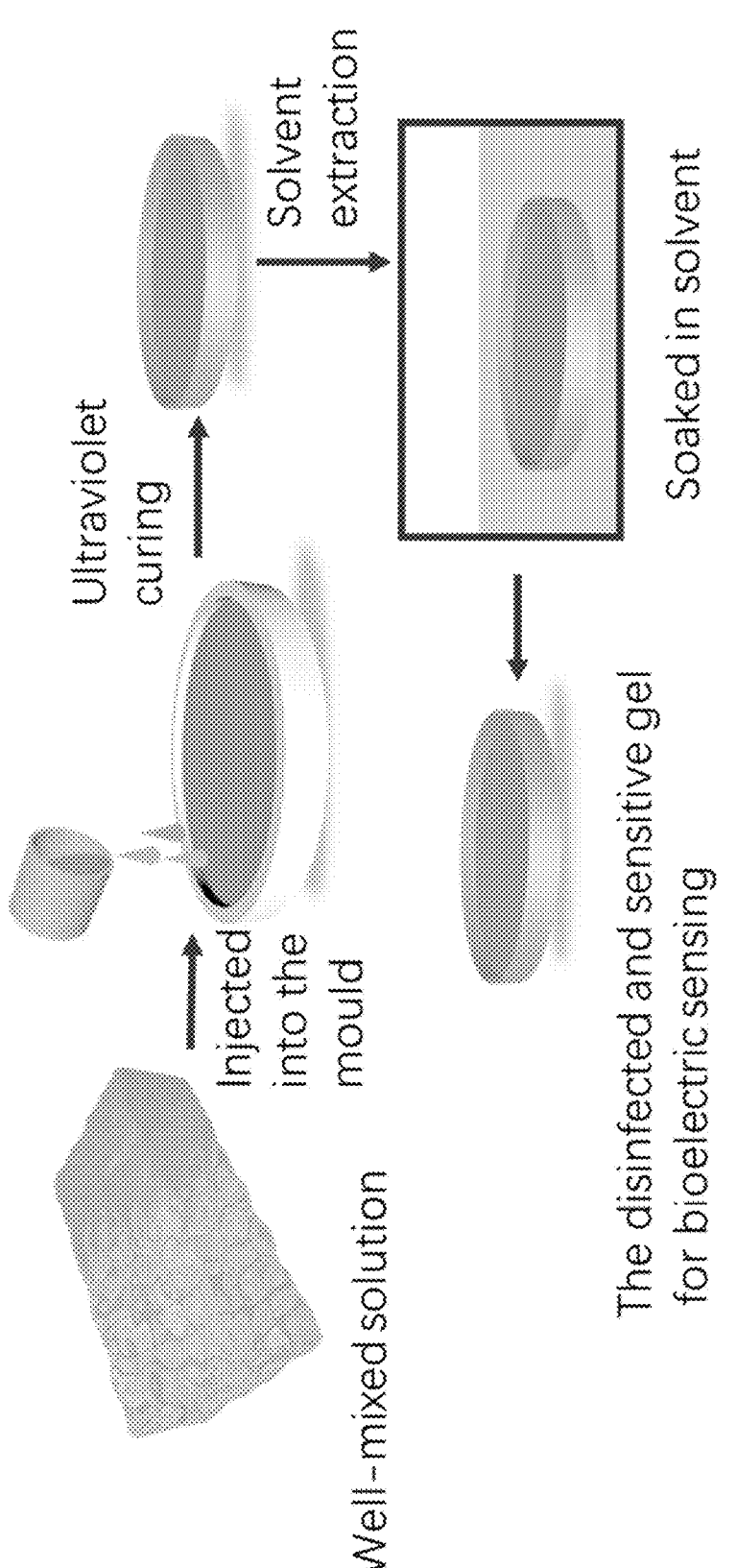
FIG. 2 is a schematic diagram of a preparation process of the interface material for virtual reality interaction prepared by the present disclosure.
Figure 3:
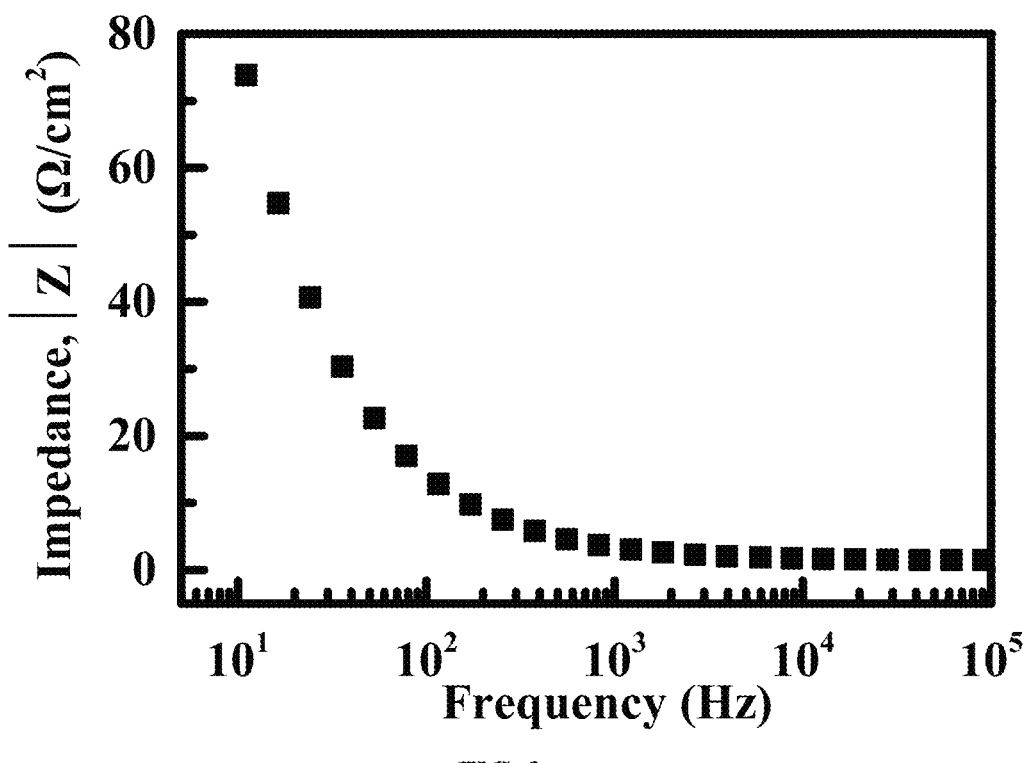
FIG. 3 is an alternating-current (AC) impedance diagram in a frequency range of $10^1$–$10^5$ Hz measured when an interface material for virtual reality interaction prepared by Example 1 is packaged between two stainless steel sheets.
Figure 4:
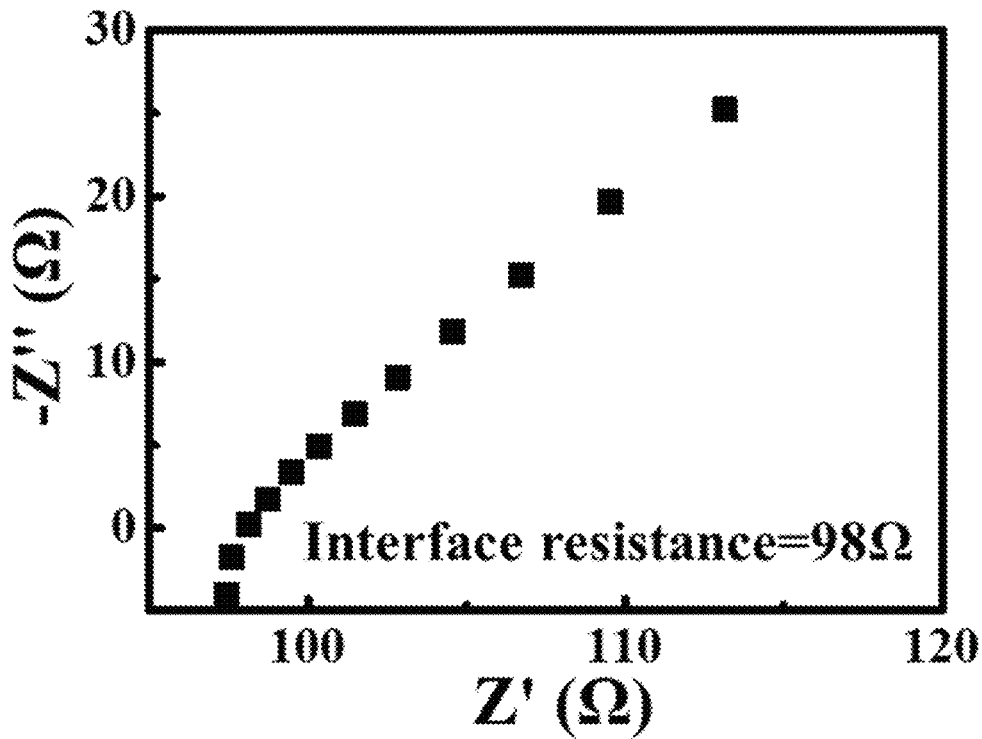
FIG. 4 is an AC impedance diagram obtained by packaging the interface material for virtual reality interaction prepared by Example 1 between a stainless steel sheet and pigskin.
Figure 5:
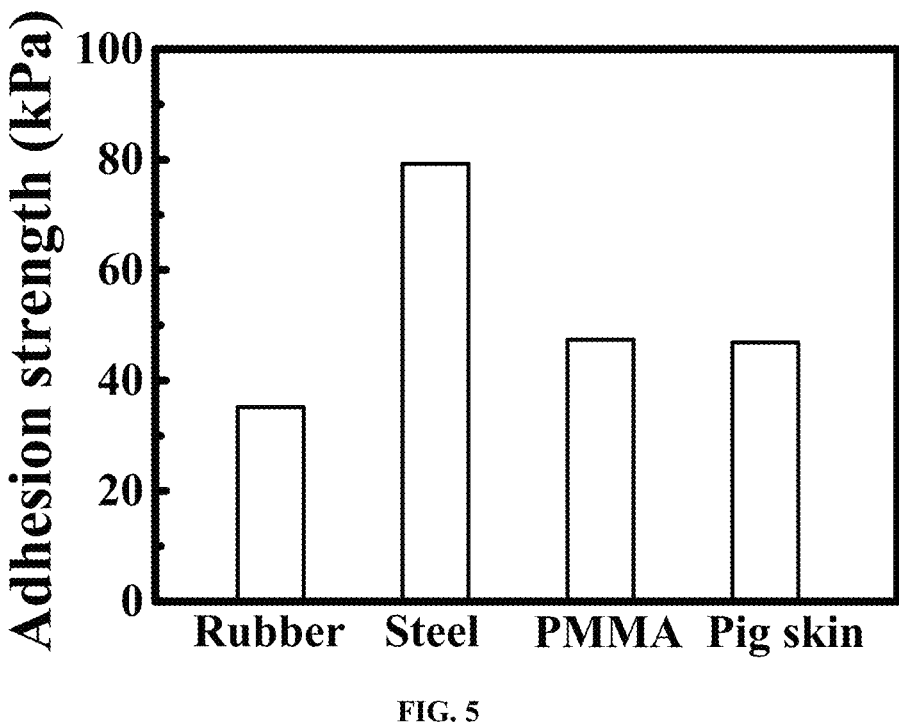
FIG. 5 shows adhesion viscosity of the interface material for virtual reality interaction prepared by Example 1 on stainless steel, rubber, polymethyl methacrylate (PMMA), and pigskin.
Figure 6:
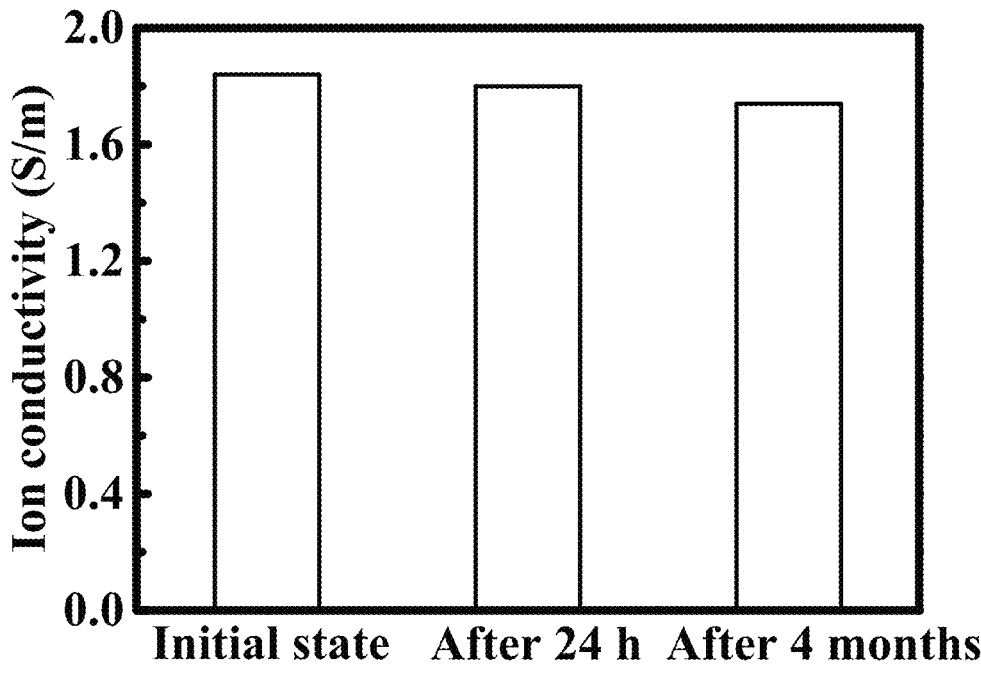
FIG. 6 shows ionic conductivity of the interface material for virtual reality interaction prepared by Example 1 in an initial state, after 24 hours of storage, and after 4 months of storage.
Figure 7:
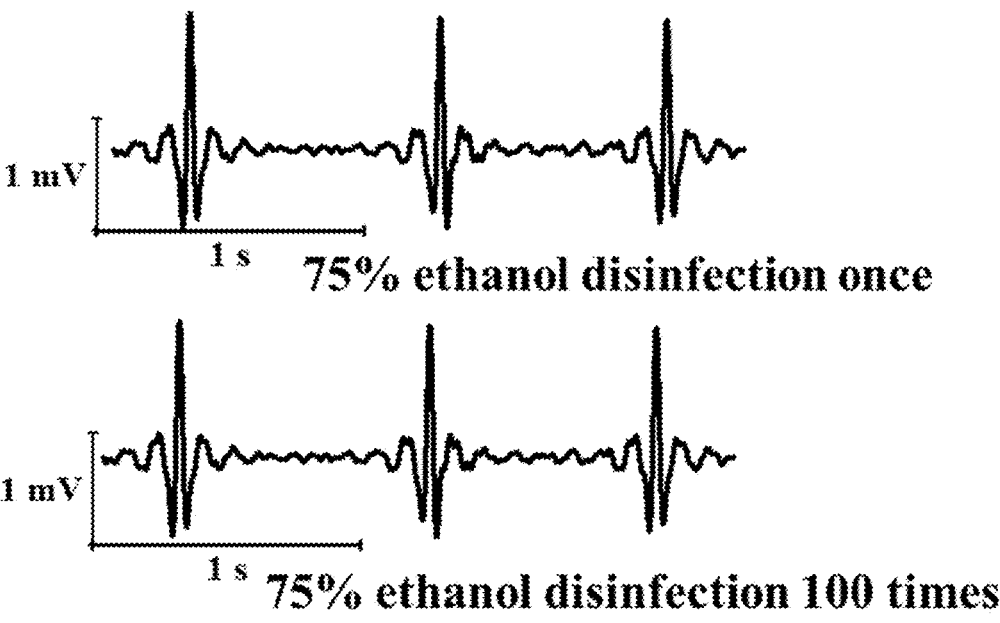
FIG. 7 is a comparison diagram of ECG signal detection results of the interface material for virtual reality interaction prepared by Example 1 after one time of disinfection with 75% ethanol and after 100 times of disinfection with 75% ethanol.
Figure 8:
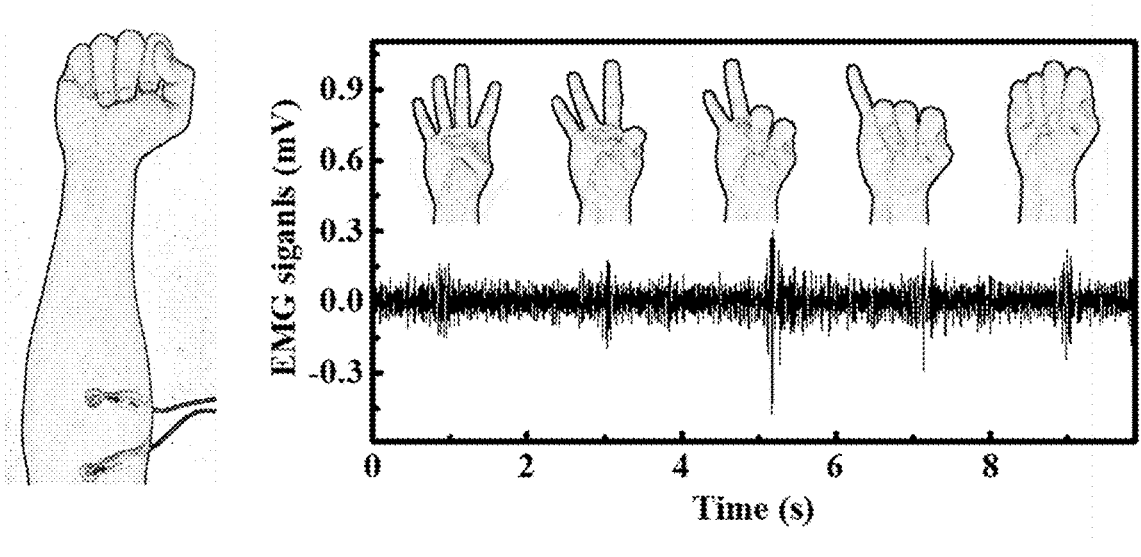
FIG. 8 shows EMG signal results measured by the interface material for virtual reality interaction prepared by Example 1.
Figure 9:
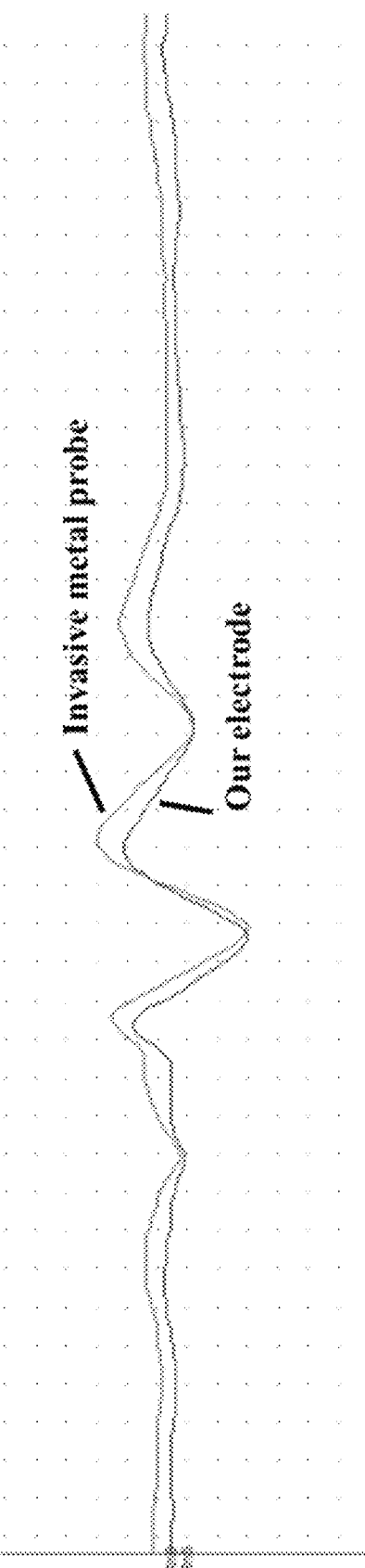
FIG. 9 is a comparison diagram of results of mouse EEG signals measured by the interface material for virtual reality interaction prepared by Example 1 and an invasive electrode.

As shown in the summary in the patent, application fields of the interface material for virtual reality interaction (detection of EEG signals, ECG signals, and EMG signals) are shown in FIG. 1, and a preparation process is shown in FIG. 2. As shown in FIG. 3, the prepared interface material for virtual reality interaction has an extremely low impedance of less than 20Ω at physiologically relevant frequencies of $10^2$-$10^5$ Hz. As shown in FIG. 4, when the interface material is used for bioelectrical signal sensing, impedance at an interface between pigskin and a stainless steel sheet is only 98Ω. FIG. 5 shows adhesion viscosity of the prepared interface material for virtual reality interaction on stainless steel, rubber, polymethyl methacrylate (PMMA), and pigskin, which are 35.2, 79.3, 47.4, and 46.9 kPa respectively. FIG. 6 shows ionic conductivity of the prepared interface material for virtual reality interaction in an initial state, after 24 hours of storage, and after 4 months of storage, which are 1.84, 1.8, and 1.74 S/m respectively. FIG. 7 shows ECG signal detection results of the prepared interface material for virtual reality interaction after one time of disinfection with 75% ethanol and after 100 times of disinfection with 75% ethanol. After 100 times of disinfection, the interface material can still obtain stable ECG signals, which shows the ECG signal detection capability and disinfectable characteristics of the interface material for virtual reality interaction. FIG. 8 shows EMG signal results measured by the prepared interface material for virtual reality interaction. The results show that when the thumb, index finger, middle finger, ring finger, and little finger are retracted in turn, the EMG signals can be measured, which shows the capability of the interface material for virtual reality interaction to detect the EMG signals. FIG. 9 is a comparison diagram of results of mouse EEG signals measured by the prepared interface material for virtual reality interaction and an invasive electrode. The results show the capability of the interface material for virtual reality interaction to detect the EEG signals, and the interface material for virtual reality interaction has the same bioelectrical detection sensitivity as the invasive electrode.

Example 2

(1) At a room temperature, 2 g of acrylamide powder was weighed and placed into a 100 mL beaker. 10 mL of deionized water was added. 0.8 g of sodium chloride, 0.05 g of tannic acid, 0.005 g of methylenebisacrylamide, and 0.05 g of a photoinitiator 12959 were added in sequence. Magnetic stirring was conducted for 1 h to obtain a transparent and clear prepolymer solution.

(2) The prepolymer solution obtained in step (1) was placed under a UV lamp with a wavelength of 365 nm and a power of 40 W for 30 min to obtain a pregel.

(3) The pregel obtained in step (2) was soaked in ethylene glycol for 1 h to obtain a disinfectable and high-sensitivity interface material for virtual reality interaction.

The appearance and material properties of the interface material for virtual reality interaction obtained in Example 2 were similar to those in Example 1. However, compared with Example 1, due to the decrease in the amount of tannic acid used, the viscosity of the interface material for virtual reality interaction was reduced to a certain extent. In addition, due to the decrease in the power of the UV lamp used, the illumination time needed to be appropriately extended, but the detection capability of the EEG signals, ECG signals, and EMG signals remained unchanged, and the disinfectable characteristics and the high-sensitivity bioelectrical signal detection characteristics remained unchanged.

Example 3

(1) At a room temperature, 2 g of acrylic liquid was weighed and placed into a 100 mL beaker. 10 mL of deionized water was added. 0.8 g of sodium chloride, 0.1 g of tannic acid, 0.005 g of methylenebisacrylamide, and 0.05 g of a photoinitiator 12959 were added in sequence. Magnetic stirring was conducted for 1 h to obtain a transparent and clear prepolymer solution.

(2) The prepolymer solution obtained in step (1) was placed under a UV lamp with a wavelength of 365 nm and a power of 45 W for 20 min to obtain a pregel.

(3) The pregel obtained in step (2) was soaked in ethylene glycol for 1 h to obtain a disinfectable and high-sensitivity interface material for virtual reality interaction.

The appearance and material properties of the interface material for virtual reality interaction obtained in Example 3 were similar to those in Example 1. However, compared with Example 1, the mechanical properties of the interface material for virtual reality interaction decreased due to the change of monomer from acrylamide to acrylic acid, but the detection capability of the EEG signals, ECG signals, and EMG signals remained unchanged, and the disinfectable characteristics and the high-sensitivity bioelectrical signal detection characteristics remained unchanged.

What is claimed is:

1. A preparation method for an interface material for virtual reality interaction, comprising:
   (1) preparing a prepolymer solution: dissolving a gel monomer, an alkali metal salt, tannic acid, 2-hydroxy-1-[4-(2-hydroxyethoxy)phenyl]-2-methylpropan-1-one, and a crosslinking agent methylenebisacrylamide in an aqueous solution to prepare the prepolymer solution;
   (2) implementing ultraviolet (UV) curing: pouring the prepolymer solution obtained in step (1) into a mold, and conducting irradiation with a UV lamp to prepare a pregel; and
   (3) implementing solvent extraction: soaking the pregel obtained in step (2) in an organic solvent for solvent extraction to obtain the interface material for virtual reality interaction, as an organogel.

2. The preparation method for the interface material for virtual reality interaction according to claim 1, wherein in step (1), the gel monomer is one or more selected from the group consisting of acrylamide, acrylic acid, sodium acrylate, and N-isopropylacrylamide.

3. The preparation method for the interface material for virtual reality interaction according to claim 1, wherein in step (1), the alkali metal salt is one or more selected from the group consisting of lithium chloride, sodium chloride, and potassium chloride.

4. The preparation method for the interface material for virtual reality interaction according to claim 1, wherein in step (1), the gel monomer has a concentration of 1-5 mol/L in the aqueous solution.

5. The preparation method for the interface material for virtual reality interaction according to claim 1, wherein in step (1), the alkali metal salt has a concentration of 0.1-3 mol/L in the aqueous solution.

6. The preparation method for the interface material for virtual reality interaction according to claim 1, wherein in step (1), the tannic acid has a concentration of 0.5-3 g/L in the aqueous solution.

7. The preparation method for the interface material for virtual reality interaction according to claim 1, wherein the UV curing is conducted through the irradiation with the UV lamp.

8. The preparation method for the interface material for virtual reality interaction according to claim 1, wherein in step (2), the irradiation is conducted at a UV lamp wavelength of 305-395 nm and a power of 20-200 W for 3-60 minutes.

9. The preparation method for the interface material for virtual reality interaction according to claim 1, wherein the solvent extraction is to soak the pregel in the organic solvent, and achieve organic solvent infiltration through spontaneous solvent extraction.

10. The preparation method for the interface material for virtual reality interaction according to claim 1, wherein in step (3), the organic solvent is one or more selected from the group consisting of ethylene glycol, glycerol, and dimethyl sulfoxide; and the soaking is conducted for 1-24 hours.

* * * * *